(12) United States Patent
Hwang et al.

(10) Patent No.: US 7,822,451 B2
(45) Date of Patent: Oct. 26, 2010

(54) APPARATUS OF MEASURING GLUCOSE CONCENTRATION BY USING OPTICAL COHERENCE TOMOGRAPHY AND METHOD OF OPERATING THE APPARATUS

(75) Inventors: In Duk Hwang, Suwon-si (KR); Kyung Ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1224 days.

(21) Appl. No.: 11/385,805

(22) Filed: Mar. 22, 2006

(65) Prior Publication Data

US 2007/0027372 A1 Feb. 1, 2007

(30) Foreign Application Priority Data

Jul. 28, 2005 (KR) .................. 10-2005-0068928

(51) Int. Cl.
 *A61B 5/1455* (2006.01)
(52) U.S. Cl. .................................... 600/316
(58) Field of Classification Search ........... 600/316, 600/322, 334, 335
See application file for complete search history.

(56) References Cited

U.S. PATENT DOCUMENTS

| 5,687,721 | A | 11/1997 | Kuhls | 128/633 |
| 5,752,512 | A | 5/1998 | Gozani | 128/635 |
| 6,064,898 | A | 5/2000 | Aldrich | 600/316 |
| 6,609,015 | B2 | 8/2003 | Lucassen et al. | 600/322 |
| 6,725,073 | B1 | 4/2004 | Motamedi et al. | |
| 6,819,950 | B2 * | 11/2004 | Mills | 600/322 |
| 2002/0077535 | A1 * | 6/2002 | Finarov et al. | 600/322 |
| 2003/0144579 | A1 * | 7/2003 | Buss | 600/300 |
| 2005/0043597 | A1 | 2/2005 | Xie | |

FOREIGN PATENT DOCUMENTS

| JP | 01-146526 | 6/1989 |
| JP | 2000-258344 | 9/2000 |
| JP | 2004-191114 | 7/2004 |
| KR | 10-2004-0039139 | 5/2004 |
| KR | 10-2004-0049007 | 6/2004 |

* cited by examiner

*Primary Examiner*—Eric F Winakur
*Assistant Examiner*—Etsub D Berhanu
(74) *Attorney, Agent, or Firm*—Staas & Halsey LLP

(57) ABSTRACT

Disclosed is an apparatus and method for measuring glucose concentration by using Optical Coherence Tomography (OCT), and more particularly, an apparatus and method for increasing the blood volume around a measurement part by using a blood concentrating device and noninvasively measuring glucose concentration of the measuring portion by using OCT. A glucose concentration measuring apparatus and method using OCT according to the invention can noninvasively measure glucose concentration by using OCT and help a user to easily measure glucose concentration.

6 Claims, 5 Drawing Sheets

APPARATUS OF MEASURING GLUCOSE CONCENTRATION BY USING OPTICAL COHERENCE TOMOGRAPHY AND METHOD OF OPERATING THE APPARATUS

CROSS-REFERENCE TO RELATED APPLICATIONS

This application claims the benefit of Korean Patent Application No. 10-2005-68928, filed on Jul. 28, 2005, in the Korean Intellectual Property Office, the disclosure of which is incorporated herein by reference.

BACKGROUND OF THE INVENTION

1. Field of the Invention

The invention relates to an apparatus and method for measuring glucose concentration by using Optical Coherence Tomography (OCT), and more particularly, to an apparatus and method for increasing the blood volume to the area where blood is being drawn using a blood concentrating device and noninvasively measuring glucose concentration of the measuring portion by using OCT.

2. Description of the Related Art

Certain lifestyles have increased adult diseases. This also has increased peoples' concerns about their health.

Diabetes is one type of disease that effects adults and juveniles. The number of people suffering from diabetes is also increasing.

Diabetes is a medical condition where the glucose or blood sugar levels are elevated, due to the lack of insulin in their body. When the blood sugar levels rise, glucose is discharged in the urine. Accordingly, diabetics need to test their blood sugar about six times a day in order to adjust the blood sugar level. Also, blood sugar is one of the most important indicators of a person's health. The normal level of blood sugar is between 70 and 110 mg/dl (mg per 100 cm$^3$). After meals, the blood sugar increases and is less than 180 mg/dl. Also, even in the case of an empty stomach, the blood sugar is greater than 60 mg/dl. However, when the blood sugar increases above the normal state, a person may become dehydrated because of frequent urination, frequent thirst, and a dry mouth. When the blood sugar falls below the normal level, a person may have a feeling of uneasiness, vertigo, fatigue, etc. Also, this decrease in blood sugar may slow brain activities and if it gets more serious, brain cells may be damaged and consequently, a person suffering from diabetes without treatment may fall into a coma or die. Most people maintain an appropriate blood sugar level and have a healthy lifestyle. However, diabetics need to monitor their blood sugar levels by regularly measuring their own blood sugar to have a healthy lifestyle.

In a conventional blood sugar measuring method, a user invasively draws blood from their body by pricking or puncturing their skin to measure glucose concentration via a glucose measuring instrument using an enzymatic method.

Currently, in the case of diabetics, blood samples must be taken with a lancet about six times a day to measure glucose concentration. Accordingly, while taking a blood sample, diabetics may have an unpleasant feeling and experience pain. Also, the use of a lancet or finger stick exposes diabetics to infectious diseases. The disadvantages of using a lancet to collect blood samples are the cost, discomfort, and inconvenience. If one uses a glucose measuring instrument, a disposable litmus paper or syringe is also necessary for testing. Because the diabetics have to purchase additional supplies, the cost increases.

To solve the problems associated with the conventional method, various methods for noninvasive glucose concentration measurement are provided.

As an example, U.S. Pat. No. 6,725,073 discusses a method for noninvasively measuring analyte concentration using Optical Coherence Tomography (OCT). The above measuring method measures analyte concentration by using skin, sclera, a lip, etc. However, if a movement interferes with the light source of the OCT apparatus, the measurement of the glucose concentration may be inaccurate.

SUMMARY OF THE INVENTION

Additional aspects and/or advantages of the invention will be set forth in part in the description which follows and, in part, will be apparent from the description, or may be learned by practice of the invention.

The invention provides a glucose concentration measuring apparatus, which can increase the blood volume around a measurement part by using a blood concentrating device and improve the accuracy of the measurement by measuring glucose concentration around the measurement part, and also can measure blood sugar and blood pressure by installing a blood pressure measuring instrument in the blood concentrating device.

The invention measures glucose concentration by using an attachable fastener to a measurement part. Accordingly, the measurement of glucose concentration is more accurate.

The invention also provides a glucose concentration measuring apparatus, which is portable by using a scan probe that is in the shape of a pen.

To achieve the above and solve the aforementioned problems in the conventional art, according to an aspect of the invention, there is provided an apparatus of measuring glucose concentration by using Optical Coherence Tomography (OCT), including: a light source; a beam splitter splitting the light generated from the light source into a first beam and a second beam; a scan probe emitting the first beam to a measurement part where blood is concentrated via a blood concentrating device and receiving at least one backscattering signal from the measurement part; a reference signal generating unit emitting the second beam to a reference mirror and generating at least one reference signal corresponding to permeation depth information of the first beam from reflected light of the reference mirror; and a glucose concentration measuring unit generating an OCT signal corresponding to the penetration depth information from an interference signal of the reference signal and the backscattering signal, and measuring glucose concentration of the measurement part by differentiating the OCT signal, wherein the blood concentrating device fastens the measurement part to concentrate blood around the measurement part.

According to another aspect of the invention, there is provided a method for measuring glucose concentration by using OCT, including the steps of: generating light via a light source; splitting the light generated from the light source into a first beam and a second beam having the same quantity of light via a beam splitter; emitting the first beam to a measurement part where blood is concentrated by a blood concentrating device and receiving at least one backscattering signal from the measurement part via a scan probe; emitting the second beam to a reference mirror and generating at least one reference signal corresponding to penetration depth information of the first beam from reflected light of the reference mirror; and generating an OCT signal corresponding to the penetration depth information from an interference signal of the reference signal and the backscattering signal, and measuring glucose concentration of the measurement part by differentiating the OCT signal, wherein the blood concentrating device fastens around the measurement part to concentrate the blood within the measurement part.

BRIEF DESCRIPTION OF THE DRAWINGS

The above and/or other aspects and advantages of the invention will become apparent and more readily appreciated from the following detailed description, taken in conjunction with the accompanying drawings of which.

DETAILED DESCRIPTION OF THE PREFERRED EMBODIMENTS

Figure 1:
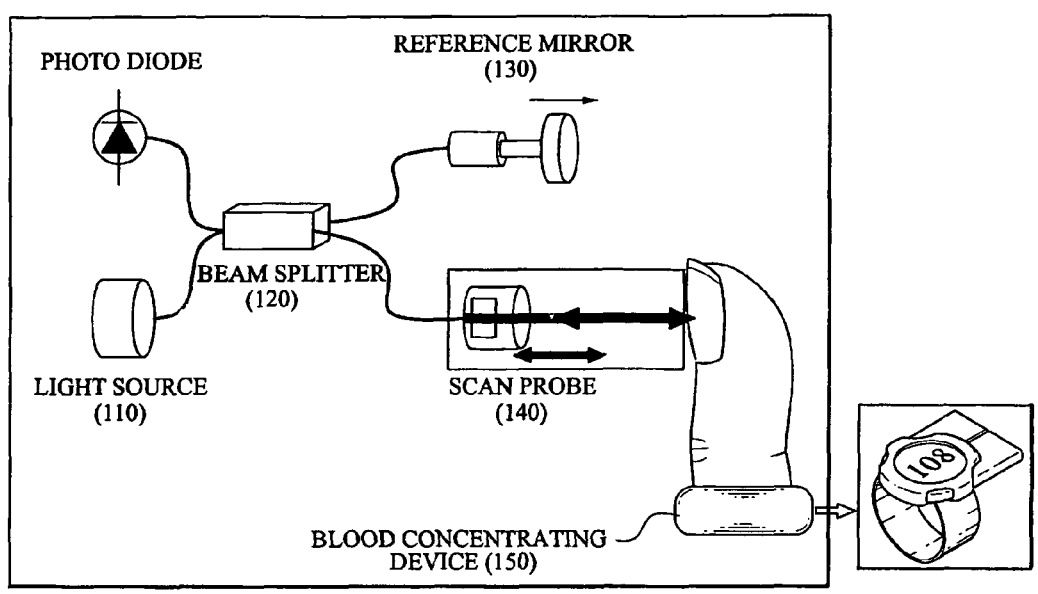
FIG. 1 is a schematic diagram illustrating a configuration of a glucose concentration measuring apparatus according to an embodiment of the invention.

Reference will now be made in detail to embodiments of the invention, examples of which are illustrated in the accompanying drawings, wherein like reference numerals refer to the like elements throughout. The embodiments are described below in order to explain the invention by referring to the figures.

FIG. 1 is a schematic diagram illustrating a configuration of a glucose concentration measuring apparatus according to an embodiment of the invention.

As illustrated in FIG. 1, a glucose concentration measuring apparatus 100 generates light via a light source 110 and splits the light generated from the light source 110 into a first beam and a second beam via a beam splitter 120. The light source 110 may be any one of a light emitting diode (LED), a super luminescent diode (SLD), a laser diode (LD) and a package LD module. A scan probe 140 receives the first beam from the beam splitter 120. Also, the scan probe 140 emits the first beam to a measurement part where blood is concentrated via a blood concentrating device 150. Also, the scan probe 140 receives at least one backscattering signal from the measurement part and transmits the received backscattering signal to the beam splitter 120.

The blood concentrating device 150 fastens around the measurement part to concentrate blood within the measurement part. The blood concentrating device 150 may constrict or, alternatively, release the surrounding area of the measurement part according to a user's manipulation. According to an embodiment of the invention, the blood concentrating device 150 further includes a small-sized blood pressure measuring instrument. Accordingly, the blood pressure measuring instrument 160 may measure ones blood pressure in conjunction with the glucose concentration measuring apparatus 100 or may be used independently.

The beam splitter 120 receives a backscattering signal from the scan probe 140 and receives a reference signal. In this instance, the second beam is emitted to a reference mirror 130 and the reference signal is reflected from the reference mirror 130. The glucose concentration measuring apparatus 100 generates an OCT signal for various depths from an interference signal of the reference signal and the backscattering signal and measures glucose concentration by differentiating the generated OCT signals.

Figure 2:
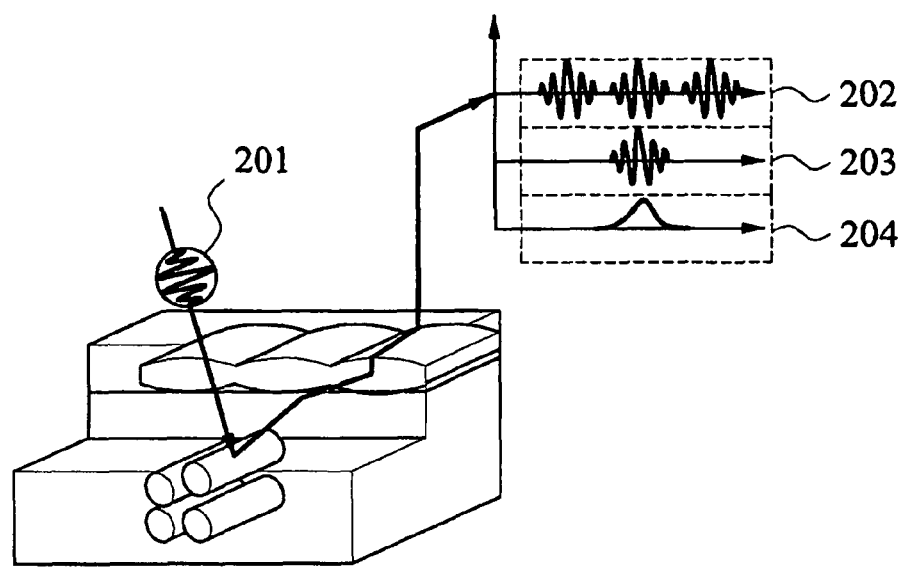
FIG. 2 is a schematic diagram for explaining the principle of Optical Coherence Tomography (OCT) used in a glucose concentration measuring apparatus according to an embodiment.

FIG. 2 is a schematic diagram for explaining the principle of Optical Coherence Tomography (OCT) used in a glucose concentration measuring apparatus according to the invention.

Referring to FIG. 2, a first beam 201 is emitted to a measurement part via the scan probe 140 of FIG. 1. Three backscattering signals 202 are received from the measurement part Since skin cells that are an area for measurement have different tissue layers and the refractive indexes of the tissue layers change, at least one backscattering signal described above is generated. To obtain a backscattering signal from a particular penetration depth where blood is concentrated among backscattering signals, a reference signal 203 corresponding to the particular penetration depth is utilized. As described above, a reference signal 203 is produced by associating the reference signal with a backscattering signal in a particular penetration depth. The produced interference signal is an OCT signal 204. The glucose concentration of the measurement part may be measured by using a slope of the OCT signal 204.

Figure 3:
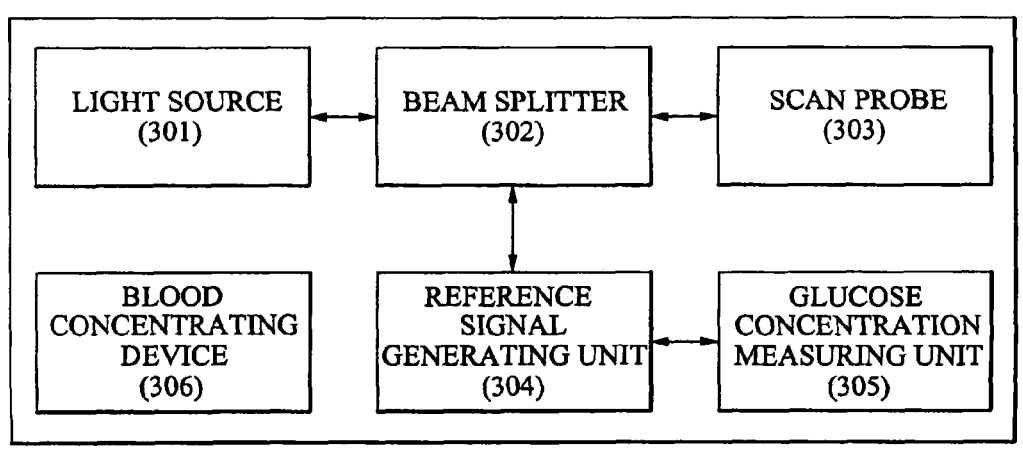
FIG. 3 is a block diagram illustrating an internal configuration of a glucose concentration measuring apparatus according to an embodiment.

FIG. 3 is a block diagram illustrating an internal configuration of a glucose concentration measuring apparatus according to an embodiment of the invention.

As illustrated in FIG. 3, a glucose concentration measuring apparatus 300 may include a light source 301, a beam splitter 302, a scan probe 303, a reference signal generating unit 304, a glucose concentration measuring unit 305, and a blood concentrating device 306.

The light source 301 generates light by using a predetermined light source, such as any one of an LED, an SLD, an LD and a package LD module.

The beam splitter 302 splits the light generated from the light source 301 into a first beam and a second beam, each having the same quantity of light. Namely, the beam splitter 302 splits the light from the light source 301 in the ratio of 50:50.

The scan probe 303 emits the first beam to a measurement part where blood is concentrated via the blood concentrating device 306, and receives a backscattering signal from the measurement part. The scan probe 303 according to an embodiment of the invention may be designed in the shape of a pen.

The blood concentrating device 306 fastens around the measurement part to concentrate the blood in the area of the measurement part. The blood concentrating device 306 may constrict or, alternatively, release the surrounding area of the measurement part according to a user's manipulation. When the first beam is emitted to the measurement part, scattering signals are generated. In this case, a part of the scattering signals are reflected back towards the direction of the emitted first beam. The scattering signal is the backscattering signal 202.

According to an embodiment of the invention, the measurement part receiving the first beam may be the epithelium of a human body capable of reducing a motion artifact, such as a fingernail. Motion artifacts can arise due to mechanical forces such as change in optical probe coupling; the patient's physiology; optical properties of the tissue; or a combination of these effects. Motion artifacts occur because of a continuous change in the position of the measurement area, such as the finger, and have an effect on the amount of light absorption of the tissue. Motion artifacts disrupt the signal between the laser and the measurement area. When the measurement part is a fingernail, a user wears the blood concentrating device 306 around the finger joint below the fingernail. In this case, the blood concentrating device 306 is fastened around the finger and constricts the finger to concentrate blood around the fingernail.

The scan probe 303 emits the first beam to the fingernail where blood is concentrated and receives a backscattering signal 202 from the fingernail. The glucose concentration measuring apparatus 300 measures glucose concentration in the fingernail by increasing the quantity of blood around the fingernail via the blood concentrating device 306. Accordingly, the glucose concentration measuring apparatus 300 may accurately measure the glucose concentration.

Figure 4:
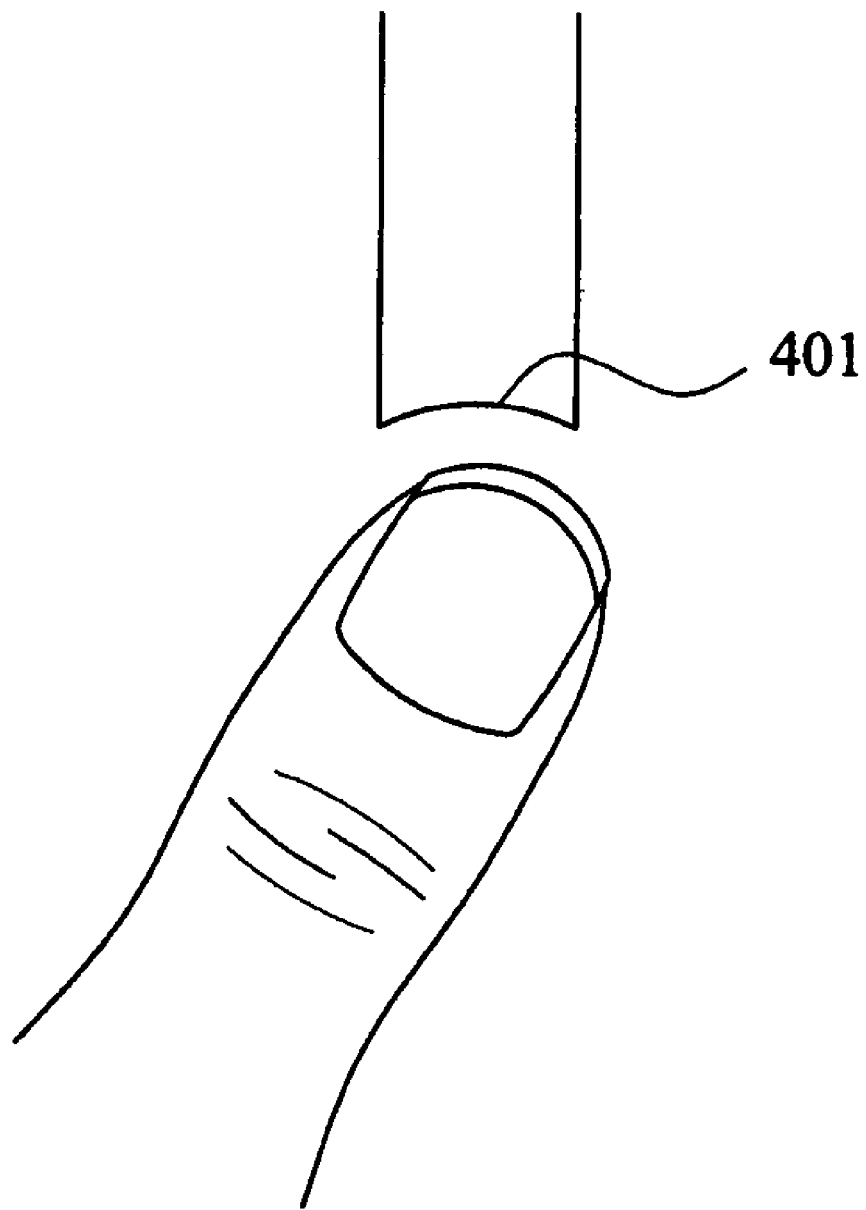
FIG. 4 is a diagram illustrating an example of the contact surface of a scan probe according to an embodiment.

According to another embodiment of the invention, as illustrated in FIG. 4, a sideface of the scan probe 303 that makes contact with the measurement part may be in the shape of a curved surface 401 corresponding to a curvature of the fingernail. This allows the scan probe 303 to be closely attached to the fingernail because a fingernail usually has a curvature. As described above, when the sideface of the scan probe 303 is in the shape of the curved surface 401 according to the curvature of the fingernail, the motion artifacts will be reduced.

According to still another embodiment of the invention, the glucose concentration measuring apparatus 300 may further include a predetermined fastener (not illustrated) that is attachable to the fingernail. The fastener attaches to the fingernail. Also, the fastener may include a cavity that is having the size of the contact surface of the scan probe 303. An example of the fastener will be described in detail with reference of FIG. 5.

Figure 5:
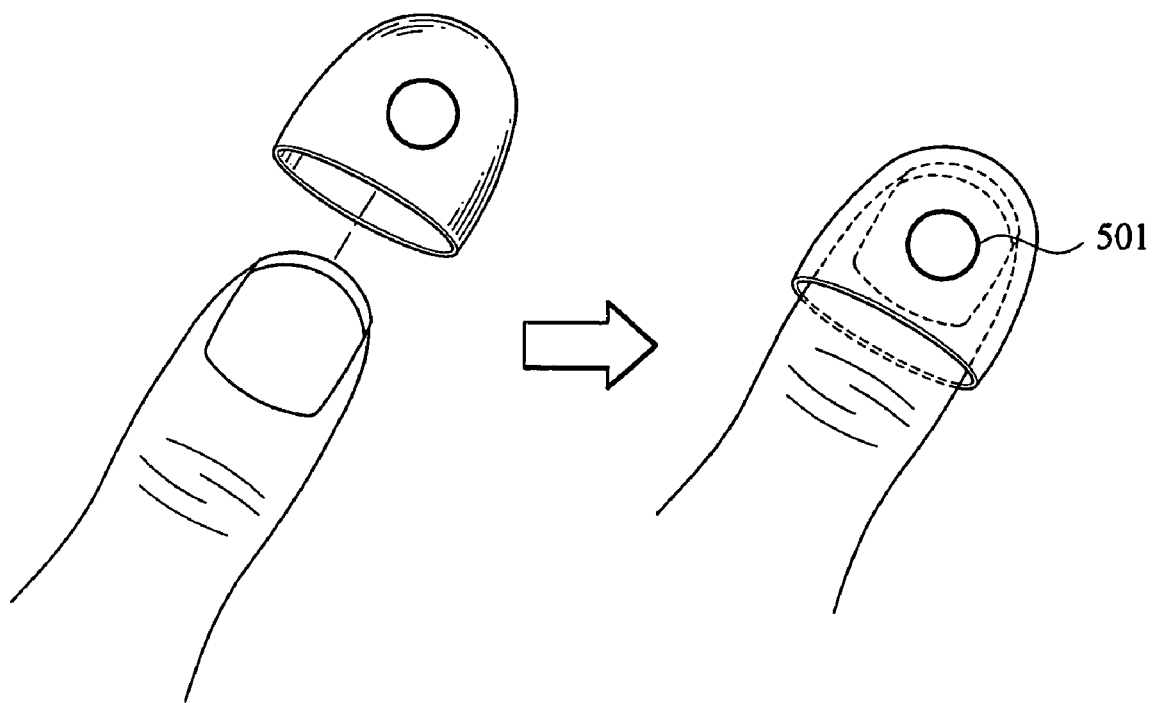
FIG. 5 is a diagram illustrating an example of a fastener according to an embodiment.

FIG. 5 is a diagram illustrating an example of a fastener according to an embodiment of the invention.

As illustrated in FIG. 5, the fastener attaches to the fingernail and includes a cavity 501 that is the size of the scan probe 303 of FIG. 3 and is in contact with the fingernail. The cavity 501 of the fastener may be positioned in place in the fingernail where the quantity of blood is concentrated. Also, the scan probe 303 makes contact with the fingernail via the cavity 501 of the fastener. Namely, since the scan probe 303 is in contact with the fingernail via the cavity 501 of the fastener, the motion of the scan probe 303 may be reduced even when a user is in motion.

The reference signal generating unit 304 emits the second beam split from the beam splitter 302 to a reference mirror. The reference signal generating unit 304 emits the second beam and generates at least one reference signal 203. In this instance, the reference signal 203 may be at least one signal that corresponds to the penetration depth information of the first beam emitted to the measurement beam from the scan probe 303. To generate at least one reference signal 203, the reference signal 203 generating unit 304 may generate at least one reference signal 203 corresponding to penetration depth information of the first beam by including a predetermined actuator and displacing the reference mirror. According to another embodiment of the invention, instead of the actuator displacing the reference mirror, the reference signal 203 generating unit 304 may strain an optical fiber connected to the reference mirror and generate the same reference signal as when displacing the reference mirror.

The beam splitter 302 receives a backscattering signal 202 generated from the scan probe 303 and a reference signal 203 generated from the reference signal generating unit 304. The beam splitter 302 transmits the combined light both of a backscattering signal and a reference signal to the PD (Photo Diode).

The glucose concentration measuring unit 305 generates an OCT signal 204 from an interference signal 203 of a reference signal and a backscattering signal 202. In this instance, the backscattering signal 202 is converted into an electrical signal and the reference signal 203 corresponds to a particular penetration depth information. Also, the glucose concentration measuring unit 305 differentiates the OCT signal and measures glucose concentration of the measurement part. The OCT signal 204 is generated because the backscattering signal is associated with the reference signal and a backscattering signal 202 and a reference signal 203 in a particular penetration depth generates interference. The reason of differentiating the OCT signal 204 is to measure the change of a slope of the OCT signal 204. Glucose concentration in the particular penetration depth may be measured by using the change of the slope. The above-described method of measuring glucose concentration by using the change of a slope of an OCT signal is already well-known. Accordingly, detailed description related thereto will be omitted.

Figure 6:
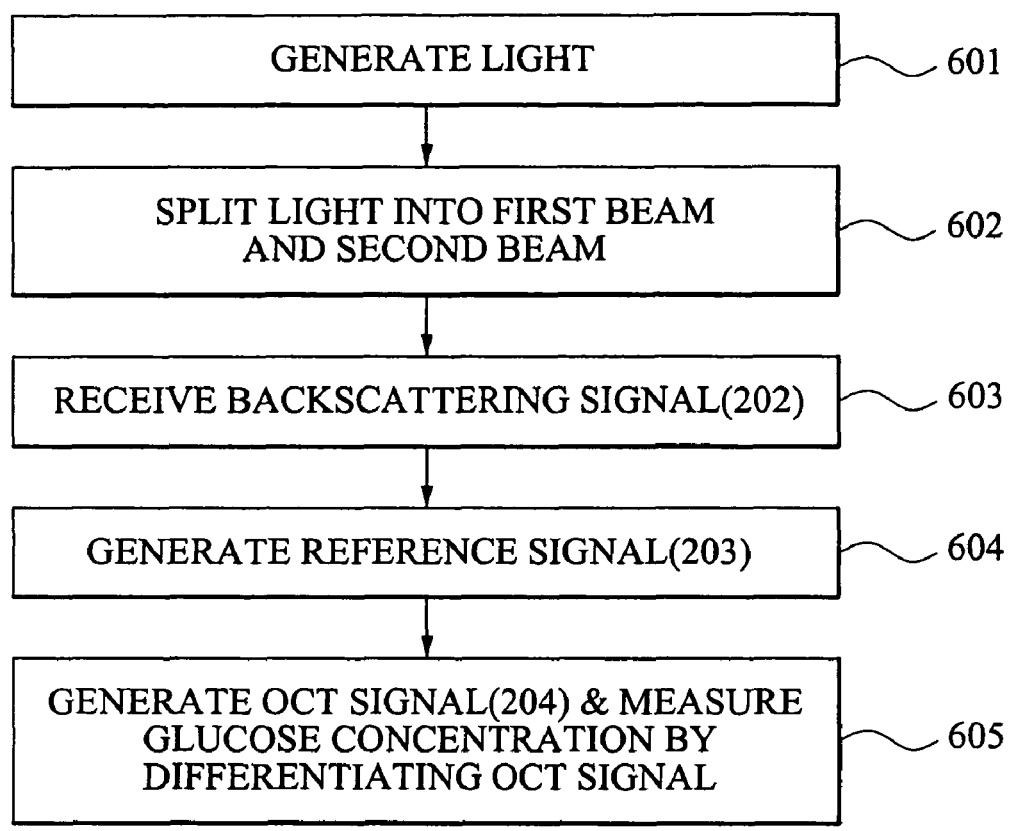
FIG. 6 is a flowchart illustrating a process of measuring glucose concentration by using OCT according to an embodiment.

FIG. 6 is a flowchart illustrating a process of measuring glucose concentration by using OCT according to the invention.

In step 601, a glucose concentration measuring apparatus generates light by using a predetermined light source.

In step 602, the glucose concentration measuring apparatus splits the light generated from the light source into a first beam and a second beam having the same quantity of light via a beam splitter.

In step 603, the glucose concentration measuring apparatus emits the first beam to a measurement part where blood is concentrated via a blood concentrating device and receives at least one backscattering signal 202 from the measurement part. In this instance, the blood concentrating device fastens around the measuring part to concentrate blood around the measurement part. The measurement part according to an embodiment of the invention may be a fingernail.

In step 604, the glucose concentration measuring apparatus emits the second beam to a reference mirror and generates a reference signal from reflected light of the reference mirror. In this case, a predetermined actuator displaces the reference mirror. According to another embodiment of the invention, step 604 may be the step of generating at least one reference signal by straining an optical fiber connected to the reference signal generating unit 304 instead of the actuator displacing the reference mirror, and generating the same reference signal as when displacing the reference mirror.

In step 605, the glucose concentration measuring apparatus generates an OCT signal 204 from an interference signal of the reference signal and the backscattering signal and measures glucose concentration of the measurement part by differentiating the OCT signal.

The glucose concentration measuring method using OCT according to the invention may be recorded in computer readable media including a program with instructions to implement various operations embodied by a computer. The media may also include, alone or in combination with the program instructions, data files, data structures, tables, and the like. The media and program instructions may be those specially designed and constructed for the purposes of the invention, or they may be of the kind that is well known and available to those having skill in the computer software arts. Examples of computer-readable media include magnetic media such as hard disks, floppy disks, and magnetic tape; optical media such as CD ROM disks; magneto-optical media such as floptical disks; and hardware devices that are specially configured to store and perform program instructions, such as read-only memory devices (ROM) and random access memory (RAM). The media may also be a transmission medium such as optical or metallic lines, wave guides, etc. including a carrier wave transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the invention.

A glucose concentration measuring apparatus and method using OCT according to the invention that can noninvasively measure glucose concentration by using OCT and help a user to easily measure their glucose concentration.

Also, according to the invention, a glucose concentration measuring apparatus, which can increase the blood volume around a measurement part by using a blood concentrating device and improve the accuracy of the measurement by measuring glucose concentration of the measurement part, and also can measure blood sugar and blood pressure by installing a blood pressure measuring instrument in the blood concentrating device.

Also, according to the invention, it is possible to more accurately measure glucose concentration by using an attachable fastener around a measurement part.

Also, according to the invention, it is possible to make a small sized glucose concentration measuring apparatus, which is portable by using a scan probe in the shape of a pen.

Although a few embodiments of the invention have been shown and described, the invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An apparatus of measuring glucose concentration by using Optical Coherence Tomography (OCT), comprising:
   a light source;
   a beam splitter splitting the light generated from the light source into a first beam and a second beam;
   a scan probe emitting the first beam to a measurement part where blood is concentrated via a blood concentrating device and receiving at least one backscattering signal from the measurement part wherein the blood concentrating device is configured to fasten around the measurement part to concentrate blood within the measurement part;
   a reference signal generating unit emitting the second beam to a reference mirror and generating at least one reference signal corresponding to penetration depth information of the first beam from reflected light of the reference mirror;
   a glucose concentration measuring unit generating an OCT signal corresponding to the penetration depth information from an interference signal of the reference signal and the backscattering signal, and measuring glucose concentration of the measurement part by differentiating the OCT signal; and
   a fastener capable of fastening around the measurement part and having a cavity the size of the contact surface of the scan probe,
   wherein the scan probe is configured to make contact with the measurement part via the cavity of the fastener.

2. The apparatus of claim 1, wherein the reference signal generating unit comprises a predetermined actuator displacing the reference mirror.

3. The apparatus of claim 1, wherein the blood concentrating device further comprises a blood pressure measuring instrument.

4. The apparatus of claim 1, wherein the measurement part is a fingernail.

5. A method for measuring glucose concentration by using Optical Coherence Tomography (OCT), comprising:
   fastening a fastener around a measurement part, the fastener having a cavity the size of a contact surface of a scan probe, the scan probe being inserted into the cavity and making contact with the measurement part;
   generating light via a light source;
   splitting the light generated from the light source into a first beam and a second beam having the same quantity of light via a beam splitter;
   emitting the first beam to the measurement part where blood is concentrated by a blood concentrating device and receiving at least one backscattering signal from the measurement part via the scan probe wherein the blood concentrating device fastens around the measurement part to concentrate the blood within the measurement part;
   emitting the second beam to a reference mirror and generating at least one reference signal corresponding to penetration depth information of the first beam from reflected light of the reference mirror; and
   generating an OCT signal corresponding to the penetration depth information from an interference signal of the reference signal and the backscattering signal, and measuring glucose concentration of the measurement part by differentiating the OCT signal.

6. The method of claim 5, wherein the measurement part is a fingernail.

* * * * *